United States Patent [19]
Atkin

[11] Patent Number: 5,817,315
[45] Date of Patent: Oct. 6, 1998

[54] RECOMBINANT VACCINE

[76] Inventor: Andrew Atkin, 56 Hampshire Dr., Nashua, N.H. 03063

[21] Appl. No.: 561,151

[22] Filed: Nov. 21, 1995

Related U.S. Application Data

[63] Continuation of Ser. No. 55,703, Apr. 29, 1993, abandoned.
[51] Int. Cl.$^6$ .......................... A61K 39/385; C07K 14/74
[52] U.S. Cl. ..................... 424/185.1; 424/193.1; 424/196.11; 424/208.1; 435/325; 435/366; 435/69.3; 435/69.7; 530/350; 530/395; 530/403
[58] Field of Search ..................... 530/395, 402, 530/403, 868, 350; 435/69.3, 252.3, 240.2, 325, 366, 69.7; 424/185.1, 193.1, 196.11, 208.1

[56] References Cited

U.S. PATENT DOCUMENTS

| | | | |
|---|---|---|---|
| 4,400,376 | 8/1983 | Sanderson | 424/88 |
| 4,478,823 | 10/1984 | Sanderson | 424/88 |
| 4,861,707 | 8/1989 | Ivanoff et al. | 435/5 |

OTHER PUBLICATIONS

Allen, H., et al., Nature 309:279–281 (17 May 1984), "Domain interactions of H–2 class I antigens alter cytotoxic T–cell recognition sites."

Guillet, J–G., et al., Nature 324:260–262 (20 Nov. 1986), "Interaction of peptide antigens and class II major histocompatibility complex antigens".

Howard, J.C., et al. P.N.A.S. (USA) 90:3777–3779 (May, 1993), "Restrictions on the use of antigenic peptides by the immune system".

Sanderson, A. R., Nature 269:414–416 (1977), "HLA 'help' for human B2–microglobulin across species barriers."

*Primary Examiner*—Thomas M. Cunningham

[57] ABSTRACT

A method for an induction of immune response against polypeptide employing antigenic presentation of said polypeptide in the form of either fusion protein with MHC product amino acid sequence or tertiary complex with MHC product on natural or artificial membrane, where said membrane may further either localize in internal compartment mediators of immune response or present membrane-bound form of said mediators on the surface of said membrane.

10 Claims, No Drawings

RECOMBINANT VACCINE

This is a continuation of application Ser. No. 08/055,703, filed Apr. 29, 1993 now abandoned.

BACKGROUND OF INVENTION

1. Technical Field of the Invention

The present invention relates, generally, to genetically engineered vaccines and use of these vaccines for induction of the specific immunity. More particularly, the present invention relates to the recombinant fusion proteins useful for induction of the cell and/or humoral immune response as well as for immunotherapy.

2. Description of the Prior Art

It is generally known that induction of specific immune response against pathogen efficiently protects animals as well as humans from disease induced by this pathogen. Such pathogens may be viruses, bacteria, parasites and neoplasia.

The crucial role of the specific protective immunity is well established. Vaccination against the common infectious agents, as it was progressively implemented during the present century, has been very important, especially for the highly contagious infections. Two major groups of vaccines include attenuated live preparations of the infectious agents and different forms of vaccinating antigens. Majority of these variants is reviewed (G. L. Ada: Vaccines, in Fundamental Immunology, ed. W. E. Paul, Raven Press, N.Y., 1989, pp. 985–1057). Recent advances in biomedical studies provided background for identification of the proteins and peptide potentially enable to induce protective immune response against various pathogens.

The major difference between attenuated live vaccines and various preparations of the potential vaccinating antigens has been understood recently. This difference relates to the different pathways of the antigen presentation during the antigen processing by host immune system. Live viral vaccines are immunologically processed through MHC class I restricted immune response inducing preferential and highly efficient T-cell-mediated immunity. At the same time soluble antigen preparations are processed through MHC class II restricted response inducing almost exclusively humoral immunity with low protective efficiency. Unfortunately, the number of infection agents do not allow the use of attenuated vaccines and various approaches were proposed to resolve the problem using inactivated pathogens, subunit vaccines based on natural proteins, recombinant proteins and synthetic peptide.

Recombinant proteins providing immune response against envelope viral proteins (U.S. Pat. No. 4,790,987), Hepatitis B Virus protein (U.S. Pat. No. 5,019,386), Fowpox Virus protein (U.S. Pat. No. 5,093,258), Herpes Simplex Virus protein (U.S. Pat. No. 4,859,587), Parainfluenza (U.S. Pat. No. 4,847,081), Melanoma-specific protein (U.S. Pat. No. 5,141,742) and many others have been disclosed. Synthetic peptide as the source of antigenically active determinants inducing immune response against pathogen were disclosed for malaria (U.S. Pat. No. 4,957,738), Hepatitis B Virus (U.S. Pat. No. 4,778,784), Human Immunodeficiency Virus (U.S. Pat. No. 4,957,737; U.S. Pat. No. 5,081,226).

In order to overcome the weak activity and low efficiency of the vaccine antigens, different approaches were used. These approaches include degradable microspheres as delivery systems (U.S. Pat. No. 5,160,745), administration of the vaccine proteins in the immobilized form (U.S. Pat. No. 5,045,320) or in the form of immobilized antigen-antibody immune complexes (U.S. Pat. No. 4,493,825), copolymerization of antigenic peptide (U.S. Pat. No. 4,957,738) and administration of the mixture of the potential vaccine with either adjuvant (U.S. Pat. No. 5,047,238; U.S. Pat. No. 4,590,181) or cytokines (U.S. Pat. No. 4,689,224). However, all these ways do not provide an efficient combination for protein or synthetic peptide vaccine. Even in vivo expression of the vaccine protein using recombinant vaccinia virus (U.S. Pat. No. 5,077,213) has failed to increase the immunological activity of the potentially active protein.

The practical use of the vaccine antigen preparations is limited by their inadequate low efficiency in induction of the broad protective humoral and/or cell immune response as compared with live vaccines. It is clear that if the difficulties encountered in the development of the individual particular vaccines could be overcome on common basis, a major advancement in the treatment of various diseases, including AIDS, could be achieved.

The ideal vaccine preparation should provide cell and humoral immune response supporting efficient protection against pathogen. Therefore, the method for vaccine development should be applied to various pathogens.

The present invention provides the method for construction of the recombinant vaccine proteins and their use for induction of the protective immune response.

DESCRIPTION OF THE INVENTION

It is, therefore, an object of the present invention to provide a common basis for development of the recombinant proteins which overcomes the disadvantages inherent in the prior art and is effective in the immunoprophylactic and immunotherapeutic treatment of infection and other diseases through induction of pathogen-specific immunity.

It is an additional object of the present invention to provide a rational method for using of recombinant vaccine proteins for a treatment of infection and other diseases when recovery of said diseases is associated with induction of the specific immune response.

Other objects and advantages of the present invention will become apparent as the description thereof proceeds.

The foregoing and related objects of the present invention are achieved by induction of the allospecific-like cell and humoral immune response against antigenic target polypeptide sequence. Said presentation of the target sequence is achieved using either [1] direct incorporation of the target sequence in the sequence of the MHC product or [2] association of the target sequence with MHC product through noncovalent binding or [3] indirect association of the target sequence with MHC product in the cluster of the membrane proteins.

Recombinant proteins containing the target amino acid sequence are expressed in suitable prokaryotic or eukaryotic genetic system. Amino acid sequences homologous to the leader peptide of eukaryotic membrane proteins should be included into the expressed sequence for direct expression of the recombinant protein on the membrane of eukaryotic cells using any recombinant expression vector. The foregoing recombinant vaccine protein is essentially presented to the host immune system in the membrane-bound form on the surface of either natural cell or artificial membrane of the natural or artificial vesicles. Said vesicles may contain cytokines and mediators necessary for the local regulation of the immune reaction.

The foregoing vaccine protein, in accordance with the present invention, should essentially include either [1a]

transmembrane amino acid sequence, [1b] amino acid sequence providing interaction with T-lymphocyte MHC product receptors and [1c] target amino acid sequence or [2a] anchor amino acid sequence, providing an association of said target amino acid sequence with MHC product and [2b] target amino acid sequence or [3a] amino acid sequence of cell membrane protein associated in membrane cluster with MHC product and [3b] target amino acid sequence or [4a] anchor structure providing association of the target sequence with cell protein in the membrane cluster with MHC product and [4b] target amino acid sequence.

[1a] Said transmembrane amino acid sequence may be either transmembrane domain of any membrane protein or amino acid sequence homologous to transmembrane region of any membrane protein.

[1b] Said amino acid sequence providing interaction with MHC product receptor may be either CD8 binding sequence derived from the amino acid sequence of the MHC class I product or CD4 binding sequence derived from amino acid sequence of the MHC class II product.

[2a] Said anchor amino acid sequence may be but are not limited to the β-2-microglobulin sequence providing interaction with MHC class I cell membrane protein, amino acid sequence of MHC class II α-chain or β-chain sequences providing interaction correspondingly with β-chain or α-chain MHC class II cell membrane proteins providing interaction with cell membrane proteins.

[3a] Said amino acid sequence may be complete or partial sequence of any membrane protein able to form a membrane cluster with MHC product including but not limited to receptors of growth factors, lymphokines and cytokines. Said sequence should essentially include the transmembrane region for membrane expression of recombinant protein.

[4a] Said anchor structure may be formed by an receptor-binding structure including but not limited to the receptor binding peptide and polypeptides of growth factors, lymphokines, cytokines and hormones.

In accordance with the present invention, the recombinant vaccine protein may be either used for immunization in association with the membrane of the eukaryotic expressing cells or purified. Purified recombinant vaccine protein should be essentially incorporated into the natural cell or artificial membrane. Foregoing recombinant vaccine protein should be expressed under the control of the corresponding genetic regulatory elements in the bacterial, yeast or eukaryotic cells including cells of the host subjected for immunization by said recombinant protein.

Foregoing recombinant protein should be essentially bound to natural or artificial membrane, incorporated into the natural or artificial membrane or expressed on the natural cell membrane. Said membrane may be artificial membrane of the liposomes, membrane of the erythrocytes and erythrocyte ghosts, membrane of nucleated cells or vesicles produced from any kind of membranes.

Recombinant vaccine protein produced by fusion of the target antigenic sequence with MHC class II sequence may be further presented on the membrane carrying membrane-bound form of Interleukin-1.

To overcome the inefficient immune response of immunocompromised host, liposomes and erythrocyte ghosts presenting recombinant vaccine protein may further contain cytokines and local mediators of immune response including but not limited to Interleukin 2, Interleukin 4 and Interleukin 5 in concentrations which are sufficient for the local induction of differentiation and proliferation of the immunocompetent cells. Further increase of the host immune response may be achieved through combination of cytokines and local immunoregulators with central regulators of immune system including but not limited to thymopoietins, thymosins and their active peptide fragments.

In accordance with the present invention, recombinant vaccine protein produced by the fusion of the antigenic target amino acid sequence with either anchor amino acid sequence or anchor structure should be essentially used as a membrane bound complex of the recombinant protein with cell membrane protein. Said complex may be produced either in vivo or in vitro. Formation of immunizing protein complex in vivo may be achieved using either in vitro expression of recombinant protein following by interaction in vivo with corresponding host membrane protein or in vivo expression of recombinant vaccine protein in cells of immunized host by appropriate expression vectors. Said vectors may be but are not limited to vaccinia virus based vectors and retroviral vectors. Said vectors are used either for infection of immunized host or infection of the cells derived from the host following by immunization of the host by infected cells. Other noninfectious genetically engineered expressing vectors may be used for transfection of the host-derived cells and expression of the vaccine protein following by immunization of the host by either transfected cells or their membranes.

Formation of the immunizing complex in vitro may be achieved by interaction of the recombinant vaccine protein through an anchor amino acid sequence or anchor structure with corresponding cell membrane protein wherein said membrane protein should be essentially bound to natural or artificial membrane, incorporated into the natural or artificial membrane or expressed on the natural cell membrane. Said membrane may be artificial membrane of the liposomes, membrane of the erythrocytes and erythrocyte ghosts, membrane of nucleated cells or membrane vesicles produced from any kind of membranes. Artificial liposomes, membrane vesicles and erythrocyte ghosts presenting immunizing complex of recombinant vaccine protein with cell membrane protein may further contain cytokines, local mediators of immune response and central immunoregulators including but not limited to Interleukin 2, Interleukin 4, Interleukin 5, thymopoietins, thymosins and their biologically active peptide fragments in concentrations which are sufficient for the local induction of differentiation, proliferation of the immunocompetent cells and immunocorrection of the host immune response.

The present invention should be understood as an artificial protein construction preferentially providing an induction of the immunological effector mechanisms through either direct or indirect association of the target antigenic amino acid sequence with MHC product amino acid sequence. For the purposes of achieving the objects of the present invention, recombinant protein constructed from MHC class I product with substitution of the hypervariable region(s) of alpha-1 and/or alpha-2 domains by target antigenic sequences, provides the most effective recombinant vaccine when folded in the complex with beta-2-microglobulin and expressed on the cells of an immunized host.

Examples of the recombinant proteins constructed in accordance with the present invention include but are not limited to Example I: fusion protein with substitution of the alpha helix in the alpha-1 domain of MHC class I protein by target amino acid sequence; Example II: fusion protein with substitution of the α-1 and α-2 domains of the MHC class I protein by target amino acid sequence; Example III: fusion protein of β-2 microglobulin anchor sequence with target sequence in the complex with MHC class I protein; Example IV: fusion protein of the β-2 microglobulin anchor sequence with target sequence in the form of membrane protein containing transmembrane domain; Example V: fusion protein with substitution of α-1 domain of the α-chain of MHC class II protein; Example VI: fusion protein with substitution of β-1 domain of the β-chain of MHC class II protein.

The following Example VII demonstrates the construction of the recombinant vaccine protein with target sequence of HIV-I env product gp41 using substitution of the α-helix in the α-1 domain of the MHC class I product by amino acid sequence derived from gp41 according to Example I.

EXAMPLE VII

1. Peripheral blood mononuclear cells are separated from the donor blood by Ficoll-Paque density centrifugation. Cells are stimulated in culture by PHA for four days and total RNA was prepared using the guanidinium thiocyanate-phenol-chloroform extraction method [Chomczynsky P., and Sacchi N. *Analytical Biochemistry* 162:156–158 (1987)].

2. cDNA corresponding to the leader peptide of the MHC class I product is prepared from the total PBMC RNA using Avian Myeloblastosis Virus reverse transcriptase and the cDNA Kit (Promega) as described by the manufacturer in a total volume of 20 μl using 15 pM of the primer SEQ ID NO:1: A AAT ACC tcT aGA GTG GGA GCC (positions from 73 to 95 relatively to the A of the ATG codon of human MHC-A,B,C, primer contains mutations to create XbaI restriction site). The reverse transcription reaction is carried out at +42° C. for 1 hour. The enzyme is inactivated at +95° C. for 15 min and the reaction mixture is adjusted to the Taq polymerase reaction containing 0.05M Tris buffer pH 8.3, 0.2 mM each of the four dNTP, 2.0 mM $MgCl_2$, 50 mM KCl, 15 pM of the upstream primer SEQ ID NO:2: TCGGAc-CCTCCCCAGACGCCGAGG ATG (positions from −24 to 3 relatively to the A of the ATG codon of human MHC-A, primer contains mutation to create BamHI restriction site) and 2.5 U of the AmpliTaq polymerase (Perkin-Elmer Cetus). The PCR reaction is subjected to 30 cycles of amplification using the following path: +95° C. for 60 sec, +50° C. for 60 sec, +72° C. for 60 sec.

3. cDNA corresponding to the MHC class I coding sequence corresponding to α-2, α-3, transmembrane and cytoplasmic domains is prepared as described in Step 1 and amplified as described in Step 2 using primers SEQ ID NO:3: CCCACAGtCgaCTGTCTCA GGC TTT (1093–1119, SalI) and SEQ ID NO:4: GC TAC TAC AtC tAG AGC GAG GCC GGG (320–345, XbaI) correspondingly.

4. PCR-amplified cDNA's are restricted by corresponding endonucleases and purified after electrophoresis in low melting agarose using Magic Prep PCR Kit from Promega according to instructions of Manufacturer. Purified fragments are cloned into the corresponding restriction sites of the pGEM3Z plasmid and reading frames are verified by sequencing.

5. HIV-I env sequence corresponding to amino acids from 535 to 582 of the gp41 is amplified using 10 cycles of PCR from the pBH10 plasmid as described in Step 2. The primers for amplification are SEQ ID NO:5: CCC tca GAG CTG TTG ATC CTT TAG G (nucleotides from 7337 to 7361 of the pBH10 sequence) and SEQ ID NO:6: GCG TCt gaG ACG CTG ACG GTA CAG GCC (nucleotides from 7176 to 7202 of the pBH10 sequence). The PCR product is digested by XbaI restriction endonuclease followed by purification, cloning into the XbaI site of the pGEM3Z and sequencing to verify the reading frame.

6. The final cloned products are combined into the single construction and recloned as BamHI-SalI fragment into the eukaryotic expression vector pTKl between BglII and XhoI sites downstream of the tk promoter and upstream of the SV40 polyadenylation signal followed by expression of the recombinant protein in transfected human lymphocytes.

While various embodiments and modifications of the invention have been described in the description, further variations will be apparent to those skilled in the art. Such modifications are included within the scope of the present invention as defined by the following claims.

---

It is claimed:

1. A recombinant vaccine protein comprising the alpha-3 domain of a MHC class I molecule, a membrane-anchoring structure and an antigenic polypeptide determinant, wherein said antigenic polypeptide determinant substitutes either a portion of the alpha-1, alpha-2 or both the alpha-1 and alpha-2 domains of said MHC class I molecule, wherein said recombinant polypeptide vaccine is expressed in membrane-bound form on the surface of a cell and wherein said antigenic polypeptide determinant is capable of interaction with T-lymphocyte receptor.

2. The recombinant vaccine protein of claim 1 wherein said antigenic polypeptide determinant is a segment of HIV gp41.

3. A recombinant expression vector capable of expressing vaccine protein of claim 1 in host cells.

4. A host cell expressing the recombinant vaccine protein of claim 1.

5. A host cell of claim 4 wherein said host cell is a lymphocyte.

6. An immunizing composition comprising the recombinant expression vector of claim 3 in a pharmaceutically acceptable form.

7. An immunogenic composition comprising the cells of claim 4 in pharmaceutically acceptable form.

8. A method of immunizing or treating a subject comprising administration of the immunizing composition of claim 6.

9. A method for immunizing or treating a subject comprising administration of the immunogenic composition of claim 7.

10. The method of claim 8 or claim 9 additionally comprising a stimulation of T cells with a mediator of immune response.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

A A A T A C C t c T    a G A G T G G G                            1 8

A G C C                                              2 2

( 2 ) INFORMATION FOR SEQ ID NO:2:

( i ) SEQUENCE CHARACTERISTICS:
        ( A ) LENGTH: 27 nucleotides
        ( B ) TYPE: nucleic acid (C) STRANDEDNESS: single
    (D) TOPOLOGY: linear (ii) MOLECULE TYPE: cDNA (xi) SEQUENCE DESCRIPTION: SEQ ID NO:2:

TCGGATcCTC CCCAGACG                                                        18

CCGAGGATG                                                                   27

(2) INFORMATION FOR SEQ ID NO:3:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CCCACAGtCg aCTGTCTC                                                         18

AGGCTTT                                                                     25

(2) INFORMATION FOR SEQ ID NO:4:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCTACTACAt CtAGAGCG                                                         18

AGGCCGGG                                                                    26

(2) INFORMATION FOR SEQ ID NO:5:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CCCtcaGAGC TGTTGATC                                                         18

CTTTAGG                                                                     25

(2) INFORMATION FOR SEQ ID NO:6:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCGTCtgaGA CGCTGACG                                                         18

GTACAGGCC                                                                   27